United States Patent
Xuan et al.

[11] Patent Number: 6,107,103
[45] Date of Patent: Aug. 22, 2000

[54] ASSAY FOR PSP94 PROTEIN

[75] Inventors: Jian W. Xuan; Joseph L. Chin, both of London, Canada

[73] Assignee: Procyon Bropharma Inc., London, Canada

[21] Appl. No.: 08/949,993

[22] Filed: Oct. 14, 1997

Related U.S. Application Data

[60] Provisional application No. 60/028,182, Oct. 15, 1996.

[51] Int. Cl.[7] ...................... G01N 33/543; G01N 33/544; G01N 33/53
[52] U.S. Cl. .......................... 436/518; 436/519; 436/501; 435/7.1; 435/7.2
[58] Field of Search ..................... 435/7.1, 7.2; 436/518, 436/519

[56] References Cited

U.S. PATENT DOCUMENTS 5,501,983  3/1996  Kilja et al. .

OTHER PUBLICATIONS von der Kamer et al. Urol. Res. 21:227–233, 1993.
Xuan et al. J. Cell. Biochem., 61: 1–13, 1996.
Catalona et al (1991) *N. Engl. J. Med.*, 324:1156–1161.
Chadwick et al (1991) *Lancet*, 338:613–616.
von der Kammer et al (1993) *Urol. Res.*, 21:227–233.
Chen et al (1995) *Clin. Chem.*, 41:1273–1282.
Davis, B.D. (1964) *Ann. N.Y. Acad. Sci.*, 121:404–427.
Xuan et al (1996) *J. Cell. Biochem.*, 63:61–73.
Xuan et al (1996) *J. Cell. Biochem.*, 61:1–13.
Xuan et al (1995) *Oncogene*, 11:1041–1047.
Stenman et al (1994) *Lancet*, 344:1594–98.
Heinz von der Kammer, et al., "Characterization of a monoclonal antibody specific for prostatic secretory protein of 94 amino acids (PSP94) and development of a two–site binding enzyme immunoassay for PSP94.," *Clinica Chimica Acta*, vol. 187 (1990), pp. 207–219.

*Primary Examiner*—Paula K. Hutzell
*Assistant Examiner*—Lin Sun-Hoffman
*Attorney, Agent, or Firm*—Dinsmore & Shohl LLP

[57] ABSTRACT

PSP94 occurs in the serum mainly as a complex with carrier protein. Determination of bound PSP94 provides an indicator of prognosis in prostate cancer and assists in diagnosis of prostate cancer in patients with borderline elevations of PSA.

12 Claims, 6 Drawing Sheets

15% non SDS-PAGE
+ Western blot

15% SDS-PAGE
+Western blot

ASSAY FOR PSP94 PROTEIN

RELATED APPLICATIONS

This application claims the benefit of U.S. provisional application No. 60/028,182 filed on Oct. 15, 1996.

FIELD OF THE INVENTION

This invention relates to methods for determining proteins which are markers for prostatic disease, including prostate tumours.

BACKGROUND OF THE INVENTION

Prostate cancer is one of the most common cancers and its incidence is increasing. It is desirable to be able to diagnose prostate cancer at an early stage when the disease is potentially curable. A number of prostate diseases, including prostate cancer, lead to increased blood levels of prostate-derived proteins such as prostate specific antigen (PSA) and these proteins serve as diagnostic markers for these diseases. Blood levels of PSA, for example, are increased when normal prostatic structure is disrupted by benign or malignant tumours or by inflammation.

Testing of PSA has increased rapidly among asymptomatic men in North America, and recommendations favouring such screening have been issued by the American Cancer Society and the American Urological Association. About 70% of patients with cancers identified by digital rectal examination, transrectal ultrasound, and needle biopsy have PSA concentrations above the cut-off values generally used. About 70–80% of abnormal PSA values in asymptomatic men, however, are false positives; only 1 in 4 men with a PSA above 4 µg/L will have prostate cancer (Catalona et al., (1991), New England Journal of Medicine, 324, 1156–1161; Chadwick et al., (1991), Lancet, 338, 613–616). The diagnostic potential of PSA measurements in serum is limited by the increase of PSA concentrations in many subjects with benign prostatic hyperplasia (BPH).

PSA has been shown to exist in serum in complexes with antichymotrypsin (ACT), $\alpha_2$ macroglobulin (AMG), protein C inhibitor and pregnancy zone protein.

When the ratio of PSA-ACT complex: total PSA was determined, 38–60% of false positives in the range 2.5–25 µg/L were eliminated, giving improved diagnostic accuracy without loss of sensitivity.

Measurement of serum PSA is not, however, totally satisfactory for diagnosis of prostate disease and the use of multiple markers has been suggested.

PSA (also known as $\alpha$-microseminoprotein) and PSP94 (prostate secretory protein of 94 amino acids, also known as $\beta$-microseminoprotein) are the two most abundant secretory proteins from prostate and PSP94 has been examined by a number of groups as a possible blood marker for prostate disease, using radioimmunoassay, enzyme immunoassay, two site immunoradiometric assay and enzyme linked immunosorbent assay.

These studies have produced conflicting results on the efficacy of serum PSP94 as a marker for prostate cancer (van der Kammer et al., (1993), Urol. Res., 21, 227–233).

SUMMARY OF THE INVENTION

The inventors have shown that most of the PSP94 in the blood occurs in a tightly protein-bound form. It is believed that previous assays have measured only free serum PSP94, which has been found by the inventors not to correlate significantly with medical outcome after treatment in prostate cancer.

This invention enables methods to determine the level of bound PSP94 or total PSP94 in biological fluids such as serum, plasma and seminal fluid. The inventors have shown that the level of bound PSP94 in serum is a better predictor of the likelihood of relapse-free survival after radiation treatment in prostate cancer than the level of free PSP94, a higher level of bound PSP94 being associated with a poorer prognosis.

SUMMARY OF DRAWINGS

Certain embodiments of the invention are described, reference being made to the accompanying drawings, wherein:

FIG. 2 15% SDS-PAGE and Western blotting analysis of serum PSP94-bound complexes in a PCa patient, after molecular sieve (Sephacryl S-200HR) separation of total serum proteins. All samples were treated with denaturing dye with 1% SDS- 1% $\beta$-mercaptoethanol and boiling. Arrow indicates the position of free PSP94 band. Non-specific binding signals with very high intensity at sizes of 25, 55 and 70 kDa were generated by the second antibody used, as demonstrated by FIGS. 4 and 5. Less exposure of lane one (seminal fluid) showed bands only for PSP94 and dimer, without background staining.

FIG. 4 15% SDS-PAGE and Western blotting analysis of serum PSP94-bound complexes further purified by protein A affinity column. Top. 15% SDS-PAGE stained by Coomassie blue Crude preparation of PSP94-bound complexes was from peak I of the molecular sieve separation of serum from a prostate cancer patient (FIG. 2). Samples taken from portions before column purification, after passing through column (not absorbed by protein A), the wash after sample loading, and the eluate, were treated with denaturing dye of 0.4% SDS- 1% $\beta$-mercaptoethanol and boiling. PSP94 lane contains ~5 ng of purified protein from human seminal plasma. Middle. Western blotting analysis of PAGE gel (top), except that ~5 ng of PSP94 was loaded. Both first antibody (1:5,00) and second antibody (1:2,000) were used. Bottom. Western blotting analysis on the same blots (middle) after complete removal of first and secondary antibodies bound (see Materials and Methods). Only second antibody (1:2,000) was used. Molecular weight standard (STD) proteins used are (from top to bottom): 43, 29, 18.4, 14.3, 6.2, 3 (kDa). Arrows indicate the position of natural PSP94.

DESCRIPTION OF THE INVENTION

Figure 1:
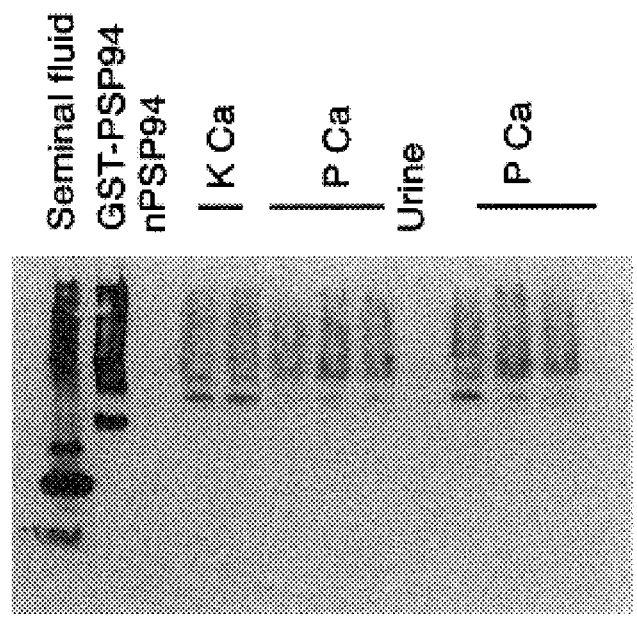
FIG. 1 shows a Western blot of PAGE-separated serum proteins detected using a polyclonal antibody against purified human seminal plasma PSP94. Panel A shows native proteins (no SDS) and Panel B shows SDS-PAGE separation. The same amount of total serum protein from 6 prostate cancer patients (PCa) and 2 kidney tumour patients (KCa) was treated with 10% glycerol and dye for native gel and with denatured dye containing 1% SDS-0.1% $\beta$-mercaptoethanol and boiling for SDS-PAGE. Samples of seminal fluid, natural PSP94 (n PSP94) and recombinant GST-PSP94 (~35 kDa) served as controls to show the position of PSP94 band (at ~16 kDa). A urine sample from one patient was also analysed.
Figure 1:
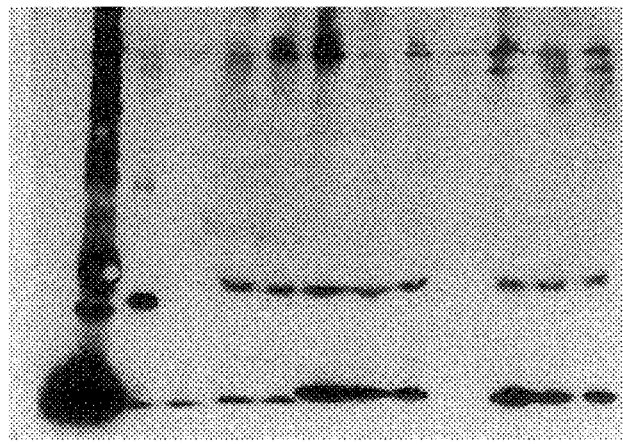

The present inventors have found that PSP94 protein exists in human blood both as free PSP94 protein and as a complex of PSP94 protein bound to carrier protein.

The bound form of PSP94 is surprisingly stable, similar to bound forms of PSA, and is very resistant to dissociation.

Furthermore, most of the PSP94 protein present in human blood is in the protein-bound form, with only a small percentage of total serum PSP94 in free form.

It has been shown by the inventors that none of 15 monoclonal antibodies and one polyclonal antibody raised using purified PSP94 as antigen could recognise bound PSP94 (data not shown). It is believed that the PSP94 epitopes recognised by these antibodies are inaccessible in the bound PSP94 complex.

Previously described assays for PSP94, therefore, measure only free serum PSP94 protein, giving a false picture of the complete status of PSP94 in blood.

The inventors have found that free serum PSP94 levels do not serve as good indicators of medical outcome in prostate cancer, and a truer picture is obtained by determining serum protein-bound PSP94 (correlation between relapse-free survival and free PSP94, on univariate analysis: p=0.8; for bound PSP94:p=0.075).

As used herein, determination or measurement of "bound PSP94" in a biological fluid refers to determination of the portion of PSP94 which occurs in the fluid bound to a carrier protein. "Bound PSP94" may be determined while still bound to carrier protein, for example, by an immunoassay using a monoclonal antibody specific for bound PSP94, as described more fully below, or by dissociation and determination of the released free PSP94.

Table II shows that higher pretreatment levels of serum bound PSP94 were associated with an increased rate of relapse following radiation treatment in patients receiving radical radiotherapy for non-metastatic (T1-T4NXMO) prostate carcinoma (multivariate analysis: p=0.022).

The present invention provides methods for determining bound PSP94 in biological fluids such as serum, plasma or seminal fluid. Measurement of serum bound PSP94 may be used as a screening test for the detection of prostate cancer or may be used, in established cases of prostate cancer, as a predictor of outcome or of likelihood of successful treatment.

The invention also provides a method of improving the accuracy of diagnosis of prostate cancer in patients presenting with a borderline elevation (<10 ng/ml) of serum PSA. It has also been shown that in patients with borderline PSA elevation, serum bound PSP94 is a good predictor of relapse-free survival after treatment, whereas PSA values did not correlate with relapse-free survival.

It is contemplated that measurement of serum bound PSP94 may be used in addition to PSA level screening, to investigate further patients with borderline PSA elevation, a large percentage of whom are known to be false negatives with respect to prostate cancer.

In one embodiment, bound PSP94 in a biological fluid, for example serum, is determined by first separating from the fluid the PSP94 which is complexed with carrier protein, followed by dissociation of the complex and determination of the released free PSP94. The complex is separated, for example, by a molecular sieve technique. The complex is then dissociated and free PSP94 separated from other components by SDS-polyacrylamide gel electrophoresis in the presence of β-mercaptoethanol. PSP94 is identified on the gel using a labelled anti-PSP94 antibody and the signal from the antibody label is quantified by comparison with known amounts of purified PSP94 run in parallel.

In a further embodiment, bound PSP94 in a biological fluid is determined by first dissociating any PSP94/carrier protein complex with a suitable dissociating agent, followed by separation and determination of the released free PSP94. For example, the released PSP94 may be separated by centrifuging the dissociation mixture through a molecular sieve/PSP94-affinity matrix column to trap the PSP94 in the matrix. PSP94 is then eluted from the matrix and determined, for example by immunoassay.

In a further embodiment, bound PSP94 is determined without dissociation from its complex with carrier protein, for example by immunoassay using an antibody which binds selectively to protein-bound PSP94 and not to free PSP94. Similar methods have been described for immunoassay of protein-bound PSA (for example U.S. Pat. No. 5,501,983 and Chen et al., (1995), Clin. Chem., 41, 1273–1282, incorporated herein by reference) and one of ordinary skill in the art can similarly determine bound PSP94.

The invention further provides a means of determining total serum PSP94 or of the relative levels of free and bound PSP94 in serum.

It has also been found by the inventors that in a few patients examined after the initiation of hormone therapy, serum bound PSP94 remained in the range found in pretreatment prostate cancer patients. This contrasts with serum PSA, the levels of which become negligible once hormone therapy is initiated. PSP94 may provide an androgen independent prostate cancer marker useful for monitoring the success or failure of hormone therapy in prostate cancer patients.

EXAMPLES

The examples are described for the purposes of illustration and are not intended to limit the scope of the invention.

Methods of protein and peptide biochemistry and immunology referred to but not explicitly described in this disclosure and examples are reported in the scientific literature and are well known to those skilled in the art.

Example 1

Free and Bound PSP94 Protein in Serum

Materials and Methods

Patient serum. Blood (~10 ml) was collected after induction of anaesthesia from patients undergoing radical prostatectomy for prostate cancer, radical cystoprostatectomy for bladder cancer and radical nephrectomy for kidney cancer. Blood samples were taken without EDTA or heparin treatment. After clotting, samples were centrifuged briefly to separate serum. For large scale purification, larger amounts of blood were collected during surgery but prior to any transfusion. Because these latter samples may contains small amounts of body fluids, 10 ml blood samples were taken before surgery and used as a control.

Purification and biotinylation of human PSP94 from semen. Human PSP94 was purified from semen samples according to the protocol reported previously (24) with the following modifications; only one round of ammonium sulfate precipitation from 30 to 70% saturation was conducted, and the use of HPLC anion exchange column was eliminated. The purification of PSP94 was characterized by overloading (~20 µg) on a 15% SDS-PAGE without any other visible bands after Coomassie blue R-250 staining. For biotinylation and detection of the labelled free form of PSP94, a Biotin-Blot Protein Detection Kit (BioRad, Mississauga, Ontario Canada) was used. The biotinylation reaction was initiated by adding 9.75 µl of NHS-Biotin (N-hydroxysuccinide biotinate in dimethylformamide, 75mM) to 1 mg PSP94 in 0.1 M sodium borate buffer pH 8.8 in a total volume of 350 µl, followed by incubation at room temperature for 4 hours. 20 µl of 1 M $NH_4Cl$ was added and incubated at room temperature for 10 min. Biotin-labelled PSP94 was desalted by 3 rounds of spinning/dilution using a Centricon-3 cartridge (Amicon, Beverly, Mass.). For detection of biotin-PSP94, ECL-Western blotting (ECL Western Blotting Kit, Amersham, Oakville, Ontario Canada) was used. The transferred blot (ECL-Hybond nitrocellulose membrane, from Amersham) with biotin-PSP94 was first reacted with avidin-HRP (horseradish peroxidase) conjugate at 1:15,000 dilution in 0.5% blocking regent (Boehringer Mannheim, Laval, Quebec Canada)/TBS (50 mM Tris-HCl pH7.5, 150 mM NaCl). ECL detection was performed according to the manufacturer's instruction (Amersham). The efficiency of biotinylation labelling of PSP94 was titrated by a dot blot test using the same procedure. Labelling efficiency was such that as low as 10 ng of the labelling mixture bound to ECL-Hybond membrane was detectable. However, using the HRP colour development reagent (BioRad), sensitivity of detection was reduced at least ten fold.

SDS-PAGE (SDS-polyacrylamide gel electrophoresis). The Laemmli system was used (25). 15% PAGE (30%T 2.67%C) was prepared according to the BioRad protocol. For samples of high density serum proteins, a high concentration of SDS (1%) and reducing agent (2.5% β-mercaptoethanol) was used to dissociate serum proteins. For the purified serum proteins, standard sample dye(25) at a final concentration of SDS (0.4%) glycerol (10%) and Tris-HCl (0.3 M pH 6.8), and reducing agent (1% β-mercaptoethanol) was used.

Native PAGE. The dicontinuous buffer system of Ornstein-Davis (Tris/chloride/glycine) was used (26). 15% polyacrylamide gel (30%T 2.67%C) was prepared using a BioRad mini-protein II system. A pH 8.8 electrode buffer was used. Serum samples were mixed with non-denaturing, bromophenol blue sample dye at a final concentration of 10% glycerol, 60 mM Tris pH6.8, and loaded directly.

Molecular sieve column purification. 1.5 ml of serum was applied to 30 ml Sephacryl S-200HR (Pharmacia, Montreal, Quebec Canada) packed in a 45×1.5 cm column (Bio-Rad Econo-column), and eluted by PBS (phosphate buffered saline). Fractions of 0.5 ml were collected at a flow rate of 0.1 ml/min. All fractions were monitored by $OD280_{nm}$. About 10 µl of sample was taken from each fraction tube for Western blotting analysis.

Protein A affinity column purification. The low salt method of protein A affinity chromatography was followed (27). Fractions of Peak I after molecular sieve separation of serum total protein were pooled, pH was added to ~8.0 by adding 1/10 volume of 1.0 M Tris (pH 8.0) and applied to a protein A column (Gibco/BRL, Burlington, Ont). The pass-through portion (with no affinity for the protein A matrix) was collected, immediately after the void volume was passed. About 5 column volumes of PBS were used for washing, and the washing solution was saved. The bound IgG portion was eluted from the column by 100 mM glycine (pH 3.0 ) in a stepwise fashion with 500 µl per fraction of 100 mM glycine (pH 3.0) and neutralized immediately in 50 µl of 1 M Tris (pH 8.0). All IgG containing fractions were monitored by $OD280_{nm}$ and pooled.

Western blotting. The chemiluminescence procedure was performed using an ECL Western Blotting Kit (Amersham) according to the protocol provided by the manufacturer. The primary antibodies were from rabbit antiserum to human PSP94 purified from seminal plasma, and were gifts from two sources, Dr. Michel Chretien (19) and Dr. S. Garde. Secondary antibodies, HRP (horse radish peroxidase) conjugated antiserum against rabbit IgG, were purchased from either Amersham or Dimension Laboratories, (Mississauga, Ontario, Canada). The first and second antibodies were diluted 5,000 and 1,000 times respectively, as described previously (21). Stripping of previous Western blotting signals was in a buffer of 50 mM β-mercaptoethanol, 2% SDS, 62.5 mM Tris -HCl pH 6.7, and incubated at room temperature for 1 hour. The stripping was tested after reaction with ECL detection buffer.

In vitro dissociation of serum proteins. Serum samples (5 µl) were treated with the following reagents (final concentration) at room temperature for 3 minutes; SDS(1%), SDS (1% ) and β-mercaptoethanol (2.5%), SDS (1%) and β-mercaptoethanol (2.5%) plus boiling, 1.5 M urea 50 mM Tris pH7.5, 3 M urea 50 mM Tris pH 7.5, 1.5 M guanidine chloride and 3 M NaCl. For purified PSP94-bound complex preparations (60 µl), treatments were: SDS (0.4%), SDS (0.4%) and β-mercaptoethanol (1%), SDS (0.4%) and β-mercaptoethanol (1%) plus boiling, 1.5 M urea 50 mM Tris pH7.5, 3 M urea 50 mM Tris pH 7.5, 1.5 M guanidine chloride and 3 M NaCl. The denatured samples were analysed immediately by native PAGE and Western blotting experiments.

RESULTS

Native and SDS-PAGE analysis of total serum proteins from prostate cancer patients. In order to differentiate various forms (free or bound forms) of PSP94 in serum, two kinds of PAGE (polyacrylamide gel electrophoresis) were employed. Native, non-SDS and non-denaturing PAGE was used to separate serum proteins in their original forms. SDS-PAGE was used with serum samples treated by reducing agent (β-mercaptoethanol) plus boiling to completely dissociate all the bound protein in serum. Two identical sets of serum samples (10 µl each) from patients undergoing radical prostatectomy and radical nephrectomy were analysed by Western blot experiments to identify PSP94. Control samples were from seminal plasma, natural (nPSP94) and recombinant GST-PSP94. Results are shown in FIG. 1. No PSP94 band corresponding to the size of the free form of purified PSP94 was found in the serum samples, when samples were run on a native, non-SDS gel (FIG. 1A). This indicates that in these sera from patients with different cancers, free PSP94 is present at very low levels. It may be less than 1 ng/10 μl, i.e. 100 ng/ml, based on comparison with the nPSP94 lane, where 1 ng was loaded. FIG. 1B is the parallel experiment but with the samples treated with SDS, β-mercaptoethanol and boiling. A free PSP94 band was observed in all tumor serum samples, suggesting that most of PSP94 present in serum is in a bound form and can be dissociated by detergent and reducing agents. No PSP94 was detectable in urine.

Molecular sieve separation of PSP94 bound complexes from serum. Since native and SDS-PAGE analyses indicated the existence of serum PSP94-bound complexes, molecular sieve (Sephacryl S-200HR) column chromatography was used to separate and purify these complexes, The elution was in PBS buffer and under non-denaturing condition. To identify bound PSP94, in FIGS. 2 and 3, fractions of peak I, the proposed PSP94-bound complexes, always eluted with or near IgG fractions in molecular sieve column chromatography. In order to purify and separate serum PSP94-bound protein complexes from IgG, peak I fractions from molecular sieve column separation were pooled and further purified by a protein A column. FIG. 4 shows the results of the analysis after one round column purification. FIG. 4 (top) shows Coomassie blue staining of PAGE analysis of this experiment. The two strong bands above PSP94 at ~25 and 55 kDa are likely to be IgG light and heavy chains, which have been dissociated by reducing agents plus boiling treatments. After protein A column chromatography, most of the IgG in peak I (before column) was in the eluate portion, and IgG remaining on the protein A column portion was low. Western blotting analysis (FIG. 4 middle) of this PAGE showed that most of the PSP94 signal was in the pass-through column portion, as compared with the PSP94 bands shown before column purification. This experiment implies that most of the serum IgG does not bind to serum PSP94 and most of serum PSP94-bound complexes showed no affinity with a protein A columns.

Figure 2:
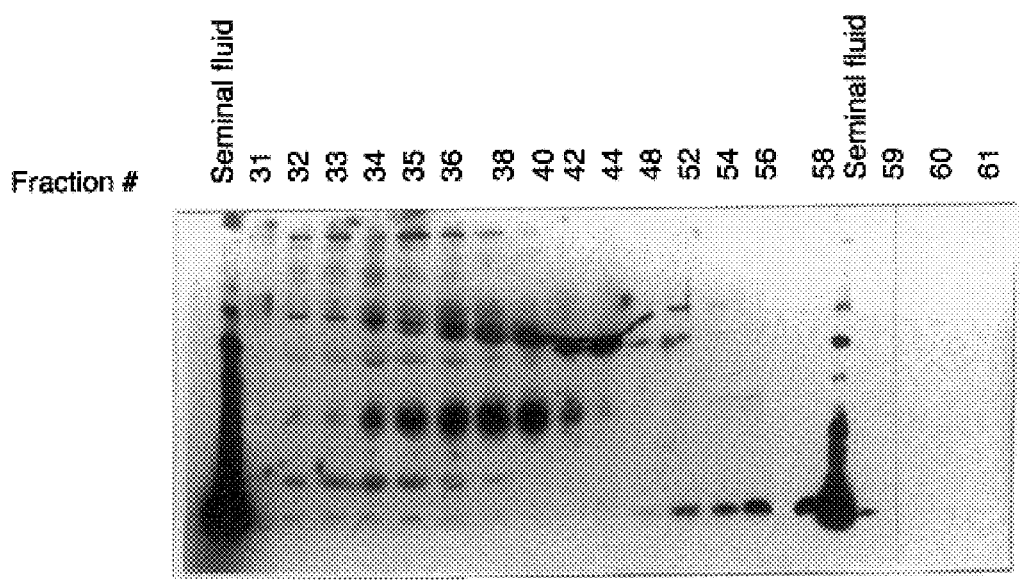

As shown in FIGS. 2, 3 and 4, Western blot analysis of serum proteins always had high background of non-specific signals. In these blots, multiple positive bands at ~25, 55, 70 kDa were repeatedly observed at higher intensity than PSP94 bands. None of the peak areas of these positive bands overlapped completely with the PSP94 peak 1. From the intensity of these bands, and also from the position of their appearances in the fractionation, we suppose that they represented albumin, and the two chains of immunoglobulins (IgG), since these two most abundant components always showed overloading bands in PAGE analysis. The results of protein A purification (FIG. 4 top and middle) also suggested that these non-specific signals might be due to the cross-reaction of two chains of IgG with polyclonal antibodies used in Western blotting experiments, since most of the IgG bands remain unchanged in the elute and were decreased in the pass-through and wash portions from the protein A column. To determine whether the first or second polyclonal antibodies were responsible for this non-specific binding, signals of Western blotting experiment of FIG. 4 (middle) was completely stripped and reacted with only second antibody (HRP-conjugated swine against rabbit IgG). The result of this control experiment is shown in FIG. 4 (bottom). Since the two experiments have the same background signal except for the PSP94 bands, we conclude the second antibody cross-reacts with human IgG. This cross-samples from fraction tubes were denatured by boiling with SDS-PAGE dye and tested by SDS-PAGE and Western blotting experiments as FIG. 1. The size of free PSP94 band is indicated by positive controls (PSP94 from seminal fluid). The specificity of rabbit antiserum against PSP94 in human seminal plasma is indicated by short time exposure of the Western blots, in which only PSP94 monomer and its remaining dimer are visible (shown in first lane, FIG. 2). FIG. 2 shows two peaks of PSP94-containing fractions in serum; the first peak (peak I) was found in fractions #32–38, with higher molecular weight, and the second peak (peak II) was located at lower molecular weight in fractions #52–59 with very strong PSP94 immunoreactive activity in this PCa patient serum. Peak I is considered to include serum PSP94-bound complexes, since peak I proteins are larger in size than serum albumin (67 kDa in fractions #44–50), which is the most abundant component in serum (60%) and appeared as an overloaded band. The fractions eluted just before the region where IgG (~150 kDa), the second most abundant (10–20%) protein in serum was eluted. The first peak has been repeatedly observed in 6 serum samples from 7 PCa patients. Peak II was observed as a strong signal in only in 1 of 7 PCa samples, and this sample was thus selected for analysis in FIGS. 2 and 3.

Figures 3A, 3B:
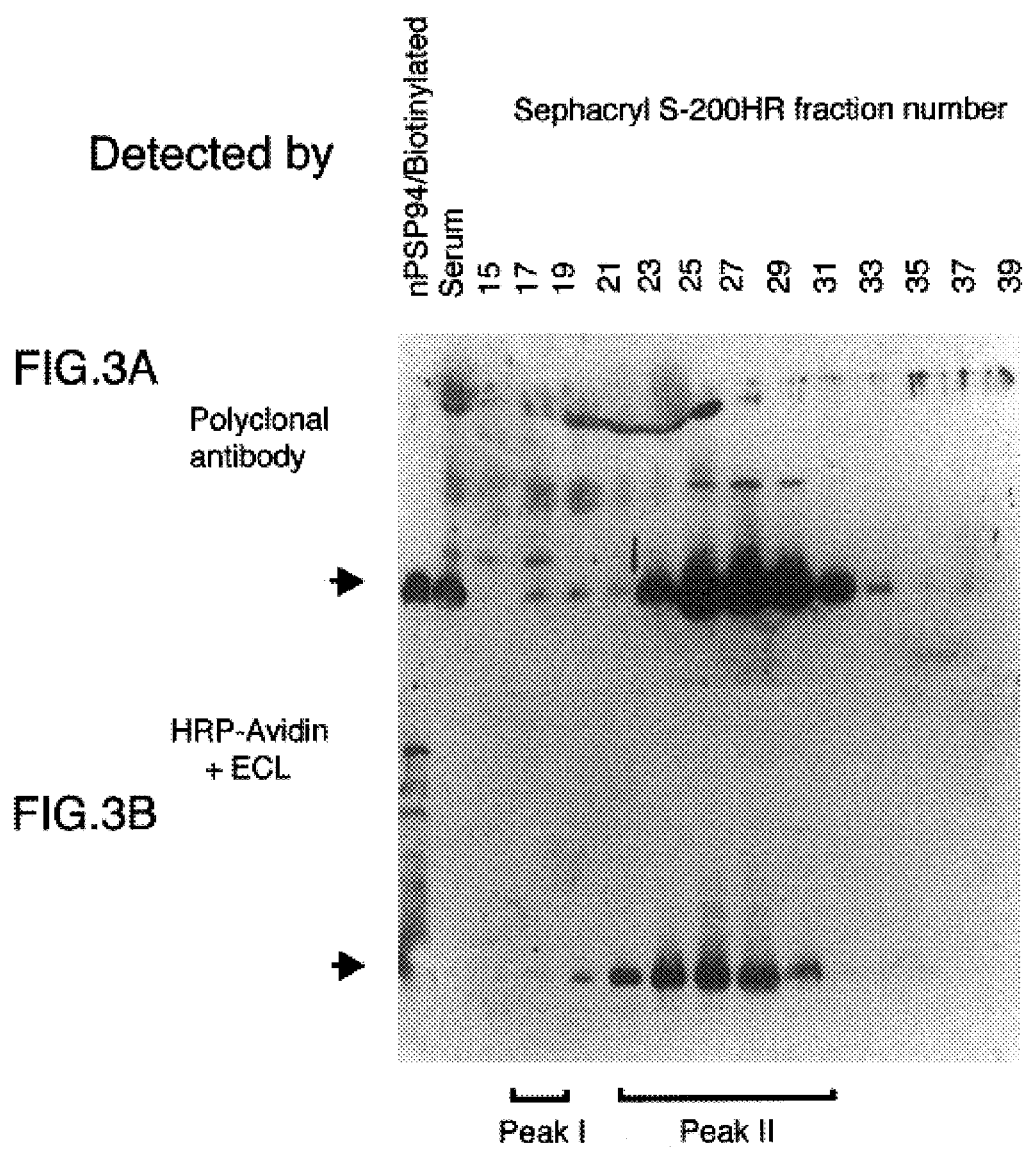
FIG. 3. Molecular sieve separation (Sephacryl S-200HR) of PSP94-serum bound complexes from the free form of PSP94 as monitored by biotinylated PSP94. Experimental procedures were as in FIG. 2. Two identical Western blots were tested by polyclonal antibody (A) and HRP-Avidin (B) separately. ECL reaction was performed according to procedures provided by the manufacturer. Arrow indicates the position of free PSP94 band.
Figure 4:
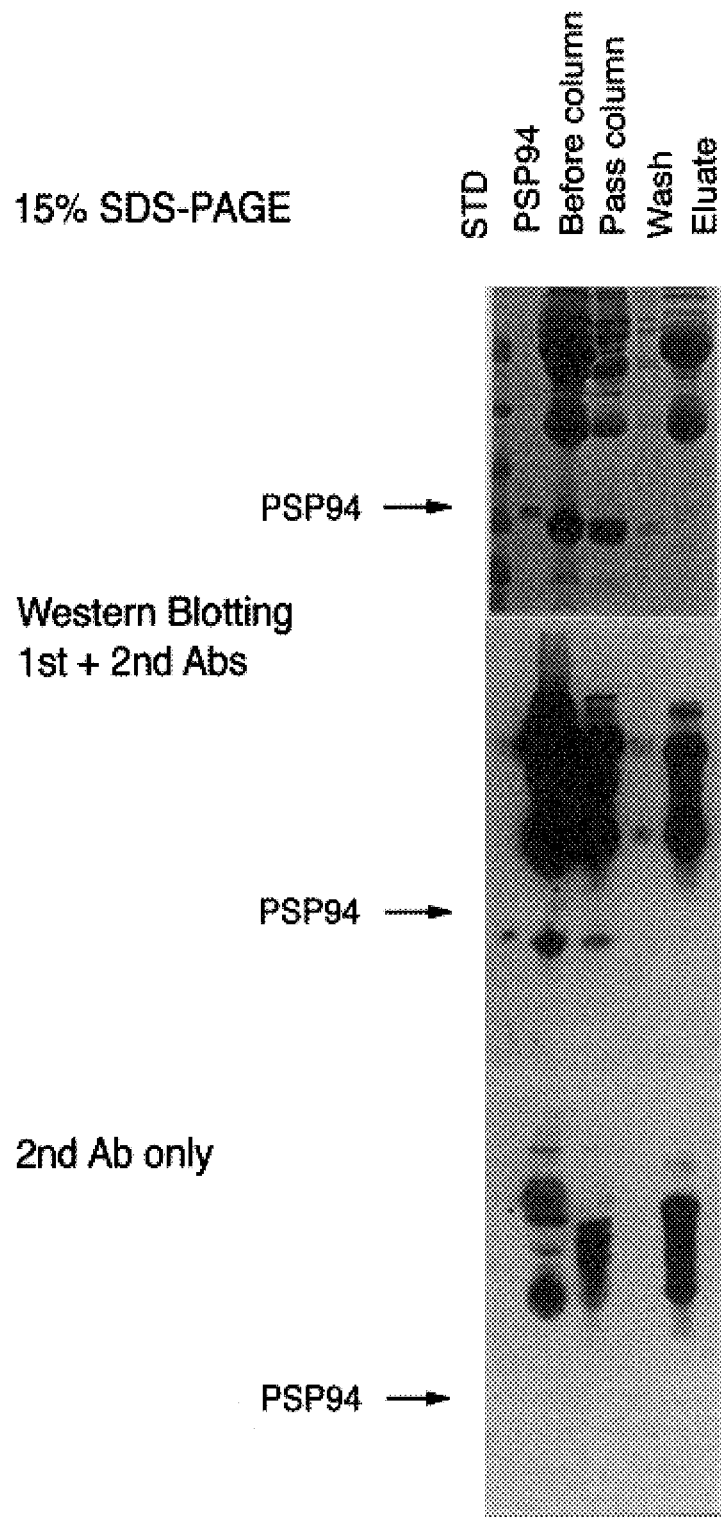

In order to determine if peak II represents free PSP94, we used biotinylated PSP94 as an indicator to monitored molecular sieve separation of total serum proteins (FIG. 3). A large amount (15 μg) of biotin labelled PSP94 was loaded together with 1.5 ml serum onto a Sephacryl S-200HR column. Fractionation and Western blotting were performed as in FIG. 2. To differentiate free (biotinylated) PSP94 from the bound form in molecular sieve chromatography, two identical blots were assessed using either polyclonal anti-PSP94 antiserum (FIG. 3A) or HRP (horseradish peroxidase)-avidin and ECL (enhanced chemiluminescence) reaction (FIG. 3B). Two peaks of PSP94 bands showed high (peak II) and lower (peak I) immunoreactivity to PSP94 polyclonal antiserum as in FIG. 2, however, the intensity of signals of peak II in FIG. 3 is higher than in FIG. 2, indicating that this peak contains both free forms of natural and biotinylated PSP94. This result is confirmed by the result of blot (FIG. 3B) reacted with HRP-avidin and ECL analysis of Biotin-PSP94. Only one peak (peak I) was detected in this blot. It is thus mostly likely that peak I represents PSP94-bound complexes.

Protein A affinity column purification of serum PSP94-bound complexes. As shown reactivity was found in two commercially available second antibodies: swine anti-rabbit and goat anti-rabbit, consistent with high levels of conservation of the IgG gene in evolution among mammals including human.

Figures 5A, 5B:
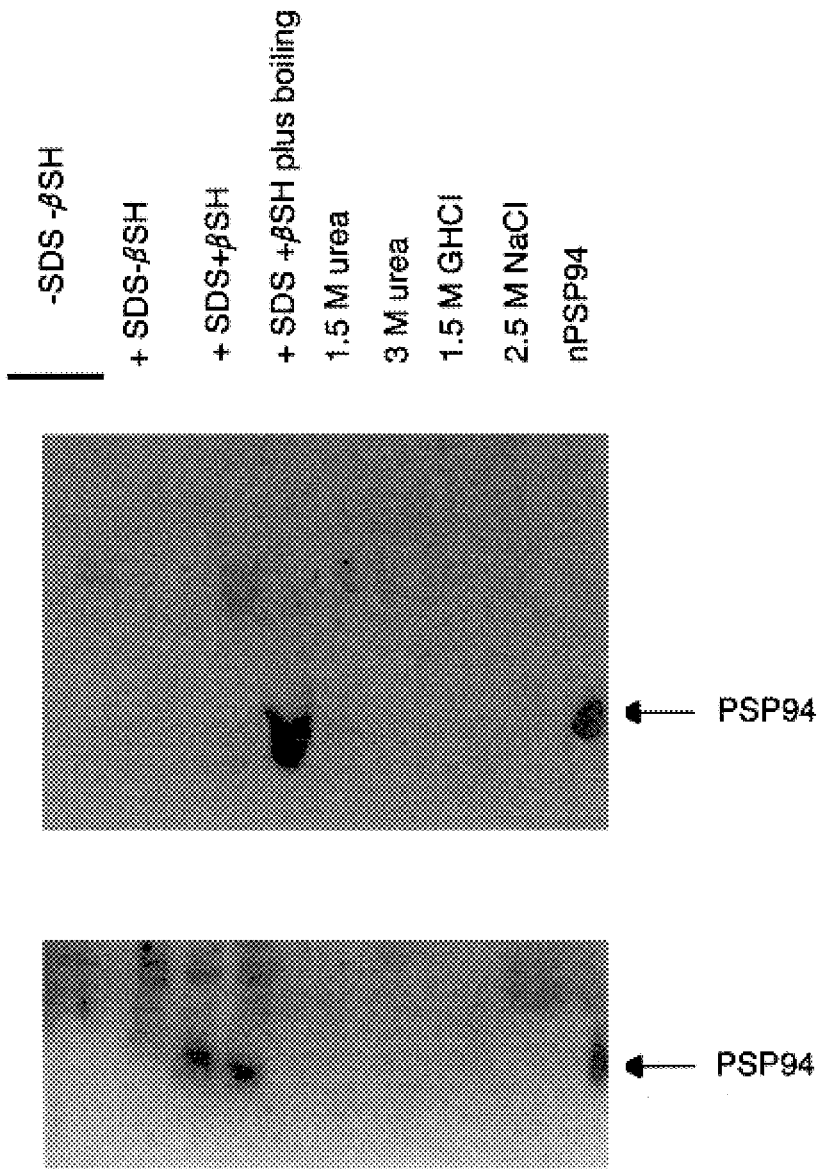
FIG. 5. 15% native PAGE and Western blotting analysis with different conditions to dissociate PSP94 from serum binding proteins (A) and crude preparations of serum PSP94-bound complexes after molecular sieve and two rounds of protein A column purification (B). For β-SH: β-mercaptoethanol; GHC1; guanidine hydrochloride; nPSP94; natural PSP94. Arrows indicate PSP94 band.

Stability of serum PSP94-bound complexes. To test the nature of the binding of PSP94 with serum proteins, serum samples from cancer patients were treated by several denaturing chemical regents: 1% SDS, 1% SDS, 1% β-mercaptoethanol, 1% SDS 1% β-mercaptoethanol plus boiling, high concentrations of urea (1.5 to 3 M), 1.5 M guanidine hydrochloride (GHCL), and 3 M NaCl. FIG. 5A shows that the binding of PSP94-bound complexes is very stable, with chemical resistance to most of these denaturing treatments. Only strong reducing reagents (1% SDS, 1% β-mercaptoethanol plus boiling) effectively dissociated the bound complexes. In order to confirm results obtained from whole serum samples, crude preparations of serum PSP94-bound complexes, purified by molecular and two rounds of protein A column purification (shown in FIG. 5B), were repeatedly tested with similar results.

Example 2

Assay for Serum Total PSP94 Protein

PSP94 Affinity Matrix:

CNBr-activated Sepharose 4B (Pharmacia) is used to immobilise an antibody specific for PSP94 protein in accordance with the manufacturer's protocol, to give a PSP94 affinity matrix. Suitable antibody can be prepared by conventional techniques using purified PSP94 protein, for example from seminal fluid, as antigen.

Spin Column Cartridge

A spin column cartridge is prepared with an upper layer of Sephadex G50 and a lower layer of PSP94 affinity matrix prepared as described above.

Method

Step 1: Dissociation

A 1 ml serum sample is treated with SDS and β-mercaptoethanol at 100° C. for about 3 minutes to dissociate PSP94 from its bound form.

Step 2: Separation of dissociated PSP94

The dissociated sample is applied to a spin column cartridge (as described above) and centrifuged briefly.

SDS and β-mercaptoethanol are trapped in the upper Sephadex layer, while the dissociated serum proteins pass through to the lower layer, where free PSP94 protein is adsorbed by the affinity matrix.

After the first centrifugation, the upper Sephadex layer is removed and the lower layer is washed extensively with phosphate-saline buffer.

The affinity matrix layer is then resuspended in a suitable buffer to elute PSP94 protein from the matrix, which is removed by a further centrifugation.

The concentration of PSP94 protein is then determined in the eluate by a conventional protein determination method, for example, immunoassay or $OD_{280}$.

Example 3

Assay of Free and Bound Serum PSP94

In order to determine the ratio of free/bound or free/total PSP94 in serum, total PSP94 can be determined as described in Example 2, free PSP94 can be determined by conventional methods, as previously described, for example, in Xuan et al., (1996) J. Cell Biochem., 63, 61–73) (which is incorporated herein by reference) and bound PSP94 can be determined by subtraction.

Example 4

Materials and Methods Patient Selection

From a group of patients receiving radiotherapy for prostate cancer at the London Regional Cancer Clinic between 1991–1992, 44 met the following criteria: T1-T4NXMO prostate cancer, treated with radiotherapy alone, pretreatment PSA available and archived pretreatment sera available for PSP94 determinations.

Patient Treatment

All patients were treated with curative intent with radiotherapy. A standard four field box technique, using high energy (18–25 Mv) photons encompassing the prostate +/− seminal vesicles was used. Patients received between 60–66 Gy in 30–33 fractions. Pelvic nodal irradiation was not routinely performed. Following treatment patients were followed at 3–6 monthly intervals with physical examination (including digital rectal examination) and PSA determinations.

Treatment Outcome

Treatment failure was defined by evidence of biochemical failure (PSA rising on two consecutive occasions or PSA >1.5 more than 1 year post radiotherapy) and/or evidence of clinical failure (any local progression on digital rectal examination or distant recurrence).

Free PSP94 Determination

Free PSP94 was measured by competitive ELISA as described in Xuan et al. (1996) J. Cell Biochem., 63, 61–73. The sensitivity of the assay was 0.17 ng. The intra assay variation was <9%, the interassay variation was <10%. Archived samples were from the same blood draw used to obtain the pretreatment PSA determinations. For the PSP94 assay, aliquots of sera were thawed and immediately assayed for PSP94 levels. We had previously determined the stability of PSP94 under these conditions by assaying aliquots of known PSP94 concentration stored under similar conditions.

Figure 6:
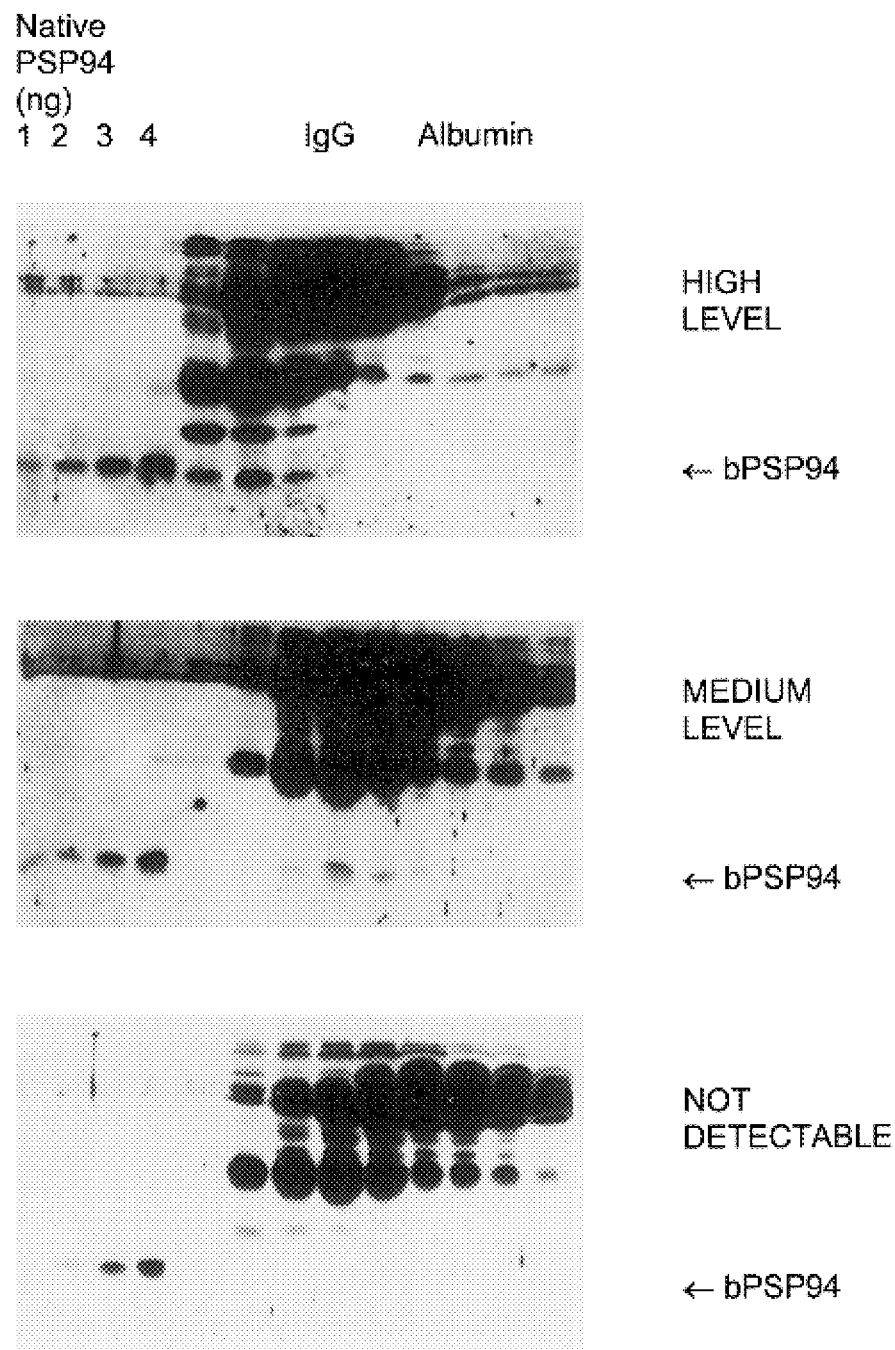
FIG. 6. ECL detection of Western blotting experiments showing semi-quantitative assay of levels of serum bound PSP94 in three prostate cancer patients with high (>1 μg/ml, top), medium (~0.5 μg/ml, middle) and low (not detectable, <50 ng/ml) levels of bound PSP94. Fractions of IgG and albumin were indicated on the top. The sequence they appeared in the elution and fractionation of molecular sieve column was from left (higher molecular weight >150 kDa for IgG) to right (smaller, ~65 kDa for albumin). In the Western blotting film, albumin fraction was shown to be overloaded (10 μl per lane), since it comprises 65% of total serum proteins. Arrow indicates positions of purified free form of PSP94.

Bound PSP94 Determination 1 ml of serum was applied to a Sephacryl S-200HR (Pharmacia, Montreal), column and eluted by PBS (phosphate buffered saline). About 10 μl of sample was taken from fractions just after the major protein (IgG and albumin) peaks. Samples were loaded onto a standard 15% SDS-PAGE using sample dye containing β-mercaptoethanol and separated by the method of Laemmli (Nature (1970), 227, 680–685). Purified human PSP94 was loaded as standard at 1, 2, 4 and 8 ng per lane in the same gel. Western blot analysis was carried out as in Example 1. Levels of serum bound PSP94 were measured according to standard PSP94 density appeared on the same ECL (Enhanced chemiluminescence) film. Due to the detection limit of the Western blotting plus ECL methods used in this assay, the sensitivity of detection of the minimum amount of serum bound PSP94 is ~50 ng per ml. FIG. 6 shows the results of this semi-quantitative assay on patient samples with high, median and low (not detectable) levels of serum bound PSP94. In 42 of the 44 patients, bound form was determined. There was insufficient serum for measurement of bound PSP94 in 2 patients.

Statistical Analysis

The following information was retrieved from the clinical records of the 44 patients: date of diagnosis, clinical stage, pretreatment PSA, tumor grade, radiation total dose and number of fractions, date of last followup, date of biochemical failure and date of clinical failure. Using a statistical software package (STATA, Stata corp,) pretreatment bound and free PSP94 levels were correlated with pretreatment PSA, tumor stage and grade. Actuarial disease control (as measured from the date of diagnosis) as a function of pretreatment PSA, grade, tumor stage and was determined by Cox univariate analysis. In addition, actuarial disease control as a function of bound and free PSP94 and bound/free PSP94 were determined by Cox univariate analysis.

Serum PSP94 levels in patients

Of the 42 patients treated, 6 were clinical stage T1, 29 stage T2 and 7 stage T3. Tumors were well differentiated in 25, moderately differentiated in 14, poorly differentiated in 3 and not graded for 2 patients. Median pretreatment PSA was 7 ng/ml (range:0.5–93) and median free and bound pretreatment PSP94 levels were 10.4 ng/ml (range: 0–79)

and 0.49 μg/ml (range:<0.05–11.2) respectively. Correlations between PSA; bound PSP94; free PSP94, tumor stage and grade are shown in Table 1. Pretreatment PSA was loosely correlated with clinical stage but not grade. Pretreatment free and bound PSP94 levels were correlated with neither tumor stage, grade, PSA, nor each other.

The 42 patients were treated with radiation to a median dose of 65 Gy (range:60–66) and followed for a median of 4.7 years (range: 3.2–5.3 years) after treatment. To date, 22 patients have failed biochemically. Of these 22, 9 also had clinical evidence of recurrent/progressive disease (4 distant failure, 5 local progression on digital rectal examination). Median time to failure was 5.2 years from diagnosis.

On Cox univariate analysis, pretreatment PSA level was a significant predictor of failure post radiotherapy; pretreatment bound PSP94 level also correlated with outcome (Table I). In contrast, free PSP94 level was not a significant predictor of failure post radiotherapy on univariate analysis when analysed as a continuous variable. To detect a possible cutoff value of PSP94 as a prognostic indicator, the univariate analysis was repeated using the median values of bound and free PSP94 as the cutoff as well as by analysing bound and free PSP94 by quartiles. No significant cutoff value of bound or free PSP94 was detected in this manner. The analysis was also repeated for the subgroups of patients with pretreatment PSA less than or greater than the median pretreatment level (7 ng/ml) in the group (Table II). Among the subgroups of patients with a favourable PSA (<median) pretreatment, bound PSP 94 level (but not PSA level) was a significant predictor of relapse survival free survival. For patients with an unfavourable PSA (>median) pretreatment, PSA level (but not bound PSP94 level) was a significant predictor of relapse free survival. On multivariate analysis, PSP94 maintained its statistical significance for the group as a whole and for the favourable PSA subgroup (Table II).

TABLE I

|  | Stage | Grades | PSA | Bound PSP94 |
| --- | --- | --- | --- | --- |
| PSA | 0.33* | −0.03 | 1 | 0.03 |
| Bound PSP94 | 0.21 | −0.02 | 0.03 | 1 |
| Free PSP94 | 0.03 | −0.003 | −0.01 | 0.18 |

*significant at p = .003

TABLE II

| Variable | Patient Group | Univariate Hazard Ratio (p value) | Multivariate Hazard Ratio (p value) |
| --- | --- | --- | --- |
| Stage | All | * | * |
| Grade | All | * | * |
| PSA | All | 0.04 (0.000) | 0.04 (0.000) |
| Bound PSP94 | All | 0.12 (0.075) | 0.17 (0.022) |
| Free PSP94 | All | * | * |
| Bound PSP94 | PSA < 7 (favourable) | 0.26 (0.047) | 0.26 (0.058) |
| PSA | PSA < 7 (favourable) | * | * |
| Bound PSP94 | PSA > 7 (unfavourable) | * | * |
| PSA | PSA > 7 (unfavourable) | 0.000 | 0.03 (0.006) |

*Not significant

We claim:

1. A method for assessing prognosis in a subject diagnosed with prostate cancer comprising:

(a) obtaining a serum or plasma sample from the subject;

(b) determining the level of bound β-microseminoprotein (PSP94) in the sample;

(c) comparing the determined level of bound PSP94 with the range of bound PSP94 levels in the serum or plasma of control subjects, wherein the higher the determined level of bound PSP94 in the prostate cancer subject, relative to control subjects, the poorer the prognosis.

2. The method of claim 1 wherein step (b) comprises (i) separating bound PSP94 from the serum;

(ii) treating the separated bound PSP94 with a dissociating agent to release free PSP94; and (iii) determining the released free PSP94.

3. The method of claim 2 wherein step (b) comprises (i) treating the serum with a molecular sieve to separate bound PSP94; and wherein steps (b) (ii) and (iii) comprise dissociating the bound PSP94 and separating the released free PSP94 by SDS-polyacrylamide gel electrophoresis in the presence of β-mercaptoethanol, followed by determining the released free PSP94 by Western blotting.

4. The method of claim 1 wherein step (b) comprises (i) treating the serum sample with a dissociating agent to release free PSP94 from any bound PSP94 in the serum;

(ii) separating the released free PSP94 from the treated sample; and (iii) determining the released free PSP94.

5. The method of claim 4 wherein step (b)(i) comprises treating the serum with sodium dodecylsulphate (SDS) and β-mercaptoethanol at about 100° C.

6. The method of claim 5 wherein step (b)(i) comprises treating the serum with 1% SDS/2.5% β-mercaptoethanol at about 100° C. for about 3 minutes.

7. The method of claim 6 wherein step (b) (iii) comprises determining PSP94 by immunoassay.

8. The method of claim 5 wherein step (b) (ii) comprises applying the treated serum sample to a two layer system comprising an upper layer of molecular sieve and a lower layer of PSP94 affinity matrix, centrifuging to trap the dissociated PSP94 in the affinity matrix layer and eluting the PSP94 from the affinity matrix layer.

9. The method of claim 3 wherein step (b) comprises determining any bound PSP94 in the serum by immunoassay using an antibody which binds selectively to bound PSP94 and not to free PSP94.

10. The method of claim 1 wherein the subject diagnosed with prostate cancer has been determined to have a serum PSA level of less than about 10 ng/ml.

11. A method for determining total β-microseminoprotein (PSP94) in a serum or plasma sample, the method comprising:

(a) providing a serum or plasma sample;

(b) treating the sample with a dissociating agent to dissociate any bound PSP94 in the fluid; and (c) determining PSP94 in the treated fluid.

12. A method for screening a subject for prostate cancer comprising:

(a) obtaining a serum or plasma sample from the subject;

(b) determining the level of bound PSP94 in the sample;

(c) comparing the determined level of bound PSP94 with the range of bound PSP94 levels in the serum or plasma of control subjects, a raised level of bound PSP94 relative to control levels being suggestive of prostate cancer in the subject.

* * * * *

UNITED STATES PATENT AND TRADEMARK OFFICE
CERTIFICATE OF CORRECTION

PATENT NO.   : 6,107,103
DATED        : August 22, 2000
INVENTOR(S)  : Jian W. Xuan and Joseph L. Chin It is certified that error appears in the above-identified patent and that said Letters Patent is hereby corrected as shown below:

<u>Title page,</u>
Item [73], Assignee, "Procyon Bropharma Inc.", should read as -- Procyon Biopharma Inc. --

Signed and Sealed this

Sixteenth Day of March, 2004

JON W. DUDAS
*Acting Director of the United States Patent and Trademark Office*